(12) United States Patent
Grosse-Puppendahl et al.

(10) Patent No.: US 10,302,810 B2
(45) Date of Patent: May 28, 2019

(54) USE OF THERMOPILES TO DETECT HUMAN LOCATION

(71) Applicant: Microsoft Technology Licensing, LLC, Redmond, WA (US)

(72) Inventors: Tobias Grosse-Puppendahl, Cambridge (GB); James Scott, Cambridge (GB); Rinku Sreedhar, Sammamish, WA (US); John Franciscus Marie Helmes, Steyl (NL); Hanchuan Li, Cambridge (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 110 days.

(21) Appl. No.: 15/420,006

(22) Filed: Jan. 30, 2017

(65) Prior Publication Data
US 2018/0217292 A1 Aug. 2, 2018

(51) Int. Cl.
*G01J 5/00* (2006.01)
*G01J 5/12* (2006.01)
*G01V 8/20* (2006.01)
*A61B 5/01* (2006.01)

(52) U.S. Cl.
CPC ............ *G01V 8/20* (2013.01); *A61B 5/01* (2013.01); *G01J 5/0025* (2013.01); *G01J 5/12* (2013.01); *G01J 2005/0048* (2013.01)

(58) Field of Classification Search
CPC .................................................. G01V 8/20
See application file for complete search history.

(56) References Cited

U.S. PATENT DOCUMENTS

| | | | |
|---|---|---|---|
| 5,982,860 A | 11/1999 | Kim | |
| 8,275,413 B1 * | 9/2012 | Fraden | H04M 1/72522 455/344 |
| 8,568,310 B2 | 10/2013 | Kahn et al. | |
| 8,884,229 B2 | 11/2014 | Barlow et al. | |
| 9,030,832 B2 | 5/2015 | Kwong et al. | |
| 9,189,073 B2 | 11/2015 | Mongia et al. | |

(Continued)

FOREIGN PATENT DOCUMENTS

CN 102331250 A 1/2012

OTHER PUBLICATIONS

Meena, et al., "Detection of position and posture of occupants using low resolution sensor", In International Journal of Computing, Communications and Networking, vol. 2, No. 1, Jan. 2013, pp. 33-35.

(Continued)

*Primary Examiner* — David P Porta
*Assistant Examiner* — Jeremy S Valentiner

(57) ABSTRACT

A method of detecting presence and location uses sensor data received from a plurality of thermopiles, each thermopile having a different field of view. In response to detecting a change in the sensor data, stored background values for each field of view are accessed and then the location of a body (e.g. a human or animal) is determined based on differences between the sensor data and sensor values predicted using a forward model and the stored background values for each field of view. Having determined the location, the stored background values are updated based on differences between the sensor data and the predicted sensor values for a body at the determined location.

20 Claims, 10 Drawing Sheets

(56) References Cited

U.S. PATENT DOCUMENTS

| | | | |
|---|---|---|---|
| 9,534,958 B1* | 1/2017 | Lhamon | G01J 5/0025 |
| 2010/0277298 A1* | 11/2010 | Leong | G01J 5/0022 |
| | | | 340/438 |
| 2012/0287035 A1 | 11/2012 | Valko et al. | |
| 2015/0130933 A1 | 5/2015 | Breuer et al. | |
| 2015/0185806 A1* | 7/2015 | S | G06F 1/3231 |
| | | | 713/323 |
| 2015/0355677 A1 | 12/2015 | Breedvelt-schouten et al. | |

OTHER PUBLICATIONS

"Infrared Gesture Sensing", http:/www.silabs.com/Support%20Documents/TechnicalDocs/AN580.pdf, Published on: 2015, pp. 1-9.

Kasama, et al., "Movement Path Estimation for Multiple Humans in a Room using Binary Infrared Sensors", In Proceedings of International Conference on Information Networking, Jan. 28, 2013, pp. 42-47.

* cited by examiner

USE OF THERMOPILES TO DETECT HUMAN LOCATION

BACKGROUND

Consumer computing devices, such as desktop computers, detect the presence of a user based on user interactions (e.g. whether a user is typing on the keyboard or moving the mouse). The same techniques are used on mobile devices, such as smartphones, and may be used to control when to dim or turn off the display. Smartphones may also use a short-range sensor (i.e. one that operates over a distance of less than 15 cm) to detect when a user is holding the smartphone to their ear and this is used to deactivate the touch-screen.

The embodiments described below are not limited to implementations which solve any or all of the disadvantages of known methods of sensing user presence and location.

SUMMARY

The following presents a simplified summary of the disclosure in order to provide a basic understanding to the reader. This summary is not intended to identify key features or essential features of the claimed subject matter nor is it intended to be used to limit the scope of the claimed subject matter. Its sole purpose is to present a selection of concepts disclosed herein in a simplified form as a prelude to the more detailed description that is presented later.

A method of detecting presence and location uses sensor data received from a plurality of thermopiles, each thermopile having a different field of view. In response to detecting a change in the sensor data, stored background values for each field of view are accessed and then the location of a body (e.g. a human or animal) is determined based on differences between the sensor data and sensor values predicted using a forward model and the stored background values for each field of view. Having determined the location, the stored background values are updated based on differences between the sensor data and the predicted sensor values for a body at the determined location.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

Figure 1:
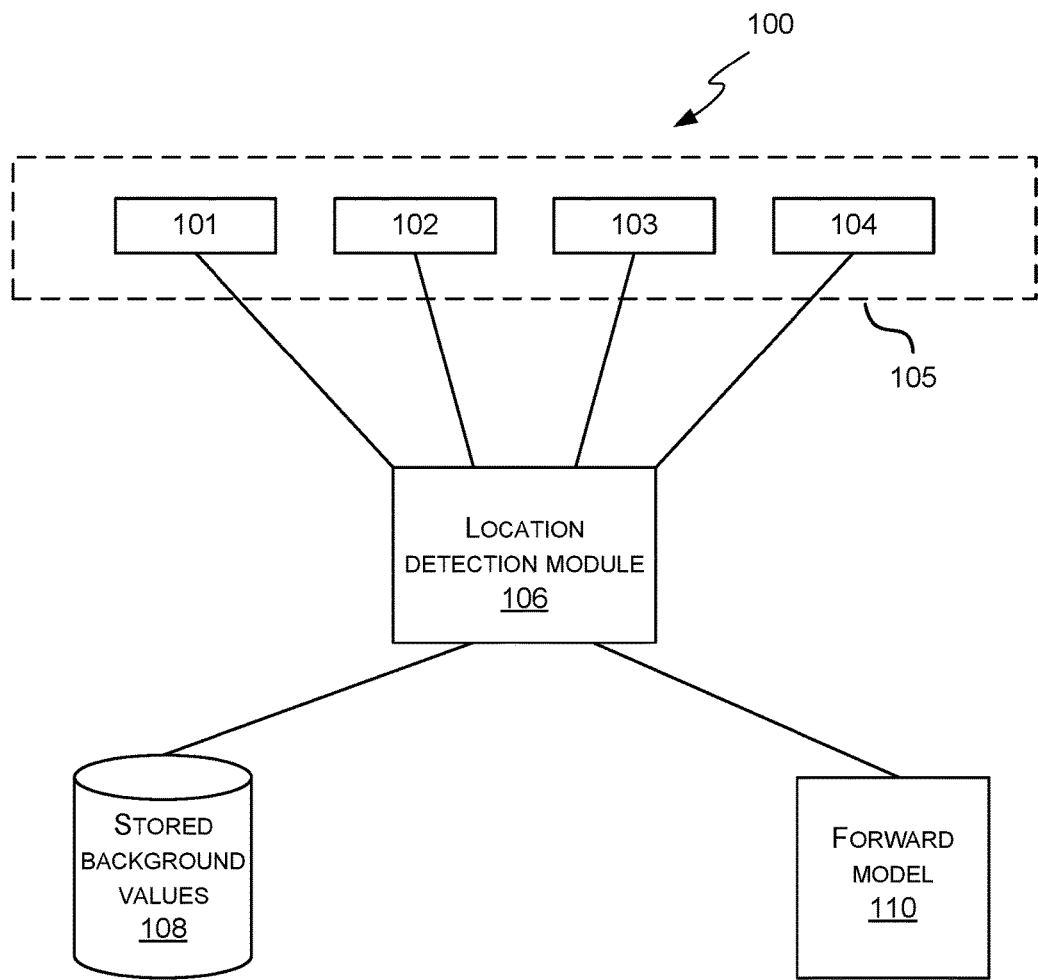
FIG. 1 is a schematic diagram of a system configured to detect the presence and location of a human.

The detailed description provided below in connection with the appended drawings is intended as a description of the present examples and is not intended to represent the only forms in which the present example are constructed or utilized. The description sets forth the functions of the example and the sequence of operations for constructing and operating the example. However, the same or equivalent functions and sequences may be accomplished by different examples.

There are many technologies that may be used to capture motion and/or determine presence of a human, including pyroelectric sensors, Doppler radar, cameras, ambient light sensors, etc. However, such devices are not typically used in consumer computing devices (e.g. desktop computers, laptops, tablet computers or smartphones) to perform presence detection at distances of more than 15 cm (e.g. distances in the range of 0.5-5 m). There are many reasons for this including the size of such devices, power consumption (particularly for battery-powered devices) and privacy concerns (e.g. in relation to continuous use of a camera or other high-resolution sensor in a computing device).

Described herein are methods of detecting both the presence and location of a body (e.g. a human or other warm body, such as an animal) using a plurality of low resolution infrared sensors, referred to as thermopiles. Thermopiles are small in size, passive (they generate a voltage dependent upon the level of infrared radiation energy), and have a wide field of view (e.g. 80-140°) and a range of up to 4 m without the use of a lens. The voltage that is generated by a thermopile is usually quite small and is digitized. The digitization circuitry that digitizes the generated voltage (and which may be integrated into the thermopile device) may be very low power (e.g. less than 200 µW). Thermopiles measure the amount of incoming infrared radiation, but the data provided (e.g. the digitized voltages) is highly ambiguous as the measured value is affected by heat sources in the environment (e.g. radiators, objects heated up by sunlight, etc.). The methods described herein address the ambiguity of the data through the use of a forward model (i.e. a predictive model) and stored background values which are updated both in the absence of a human in the field of view and when there is a human in the field of view.

The methods described herein generate a probability map for the location of a body (e.g. a human or other warm body, such as an animal). The location which is detected based on the probability map comprises an angular position of the body relative to the plurality of thermopiles (e.g. a one-dimensional or two-dimensional angular position, depending on the sensor arrangement used) and optionally also a distance of the body from the plurality of thermopiles. In examples where both an angular position and a distance is determined, this may alternatively be expressed in other ways, e.g. in the form of an (x,y,z) location. In various examples, the methods described herein may provide higher dimensional predictions, such as additionally inferring one or more of: body temperature, the height and/or pose of the body (e.g. sitting/standing/height). In various examples, the methods may predict the type of body (e.g. human/animal) based on the inferences made (e.g. based on the height and/or pose).

As described in more detail below, the presence and location of a body (e.g. a human or other warm body, such as an animal) is detected by analyzing sensor data received from a plurality of thermopiles which each have a different field of view and where, in many examples, the different fields of view are partially overlapping (e.g. such that for each thermopile, the field of view of the thermopile partially overlaps the field of view of another one of the plurality of thermopiles). In response to detecting a change in the sensor data (e.g. received from one or more of the plurality of thermopiles), a location of a body is determined by reducing (e.g. minimizing) the differences between the sensor data and sensor values predicted using the forward model and the stored background values for each field of view. Having determined the most likely location of a body (e.g. in terms of an angle and optionally a distance), any difference between the predicted sensor values (from the forward model with a body at the determined location) and the received (i.e. actual) sensor data may be used to update the stored background values for one or more of the fields of view.

The methods described herein detect both the presence and location of a body (e.g. a human) in a manner which is efficient in terms of space (e.g. size of sensors), power consumption (e.g. compared to computationally expensive algorithms for cameras), and computational power (e.g. such that the methods may be implemented on an embedded device). In contrast to systems which use radar or ultrasound, no wave emissions are used and this reduces the power consumption, eliminates the needs to conform to RF regulations or standards and also alleviates many installation considerations (e.g. where to place the sensor with conductive structures, acoustic resonances, etc.). As thermopiles rely on body heat, the methods described herein work irrespective of whether the environment is light or dark. The use of thermopiles avoids the privacy concerns associated with many other methods for detecting presence (e.g. because of the low resolution of the sensors). Furthermore, as the methods can be used to detect presence, this makes it easier to recognize people who are sitting and hence are not moving.

As detailed above, the methods described herein generate a probability map for the location of a body (e.g. a human). This probability map may, in various examples, be fed into time-based filters such as Kalman or particle filters, since they can use the full information to result in more accurate tracking over time. The generation of a probability map also aids fusion of the results with data from other sensors.

The methods described herein may, for example, be implemented in consumer computing devices (e.g. desktop computers, laptops, tablet computers, games consoles or smartphones), displays (e.g. televisions or computer monitors), wearable devices (e.g. smart watches, fitness tracking device or headphones), embedded devices (e.g. wireless sensor nodes, e.g. for home automation or indoor localization), voice assistants (which may not comprise a display), security applications, people/animal tracking devices, etc.

Having determined the location using the methods described herein, the determined location is output and may be used (e.g. within another part of the device performing the methods described herein or within a separate device) to control or otherwise affect the operation of a device (e.g. the device performing the methods described herein or a separate device). For example, the determined location may be used to control an operating mode of the device. In various examples, the determined location may be used to control whether a display device is switched on or off or controlling brightness of the display device, both of which may reduce the power consumption of the device. In various examples, the determined location may be used to switch a device between modalities like audio and visual output (e.g. based on proximity or approaching angle) and this may increase accessibility. In various examples, the determined location may be used to control what content is displayed on the display device and/or how that content is displayed, e.g. to change the font size of text depending upon the separation of the person from the display, to increase readability and hence accessibility. In various examples, the determined location may be used to provide an interactive experience, e.g. by determining a series of locations over time and using this motion (or lack thereof) as an input to a computing device (e.g. to control the operation of software running on the device or as an input to a computer game).

Figure 2:
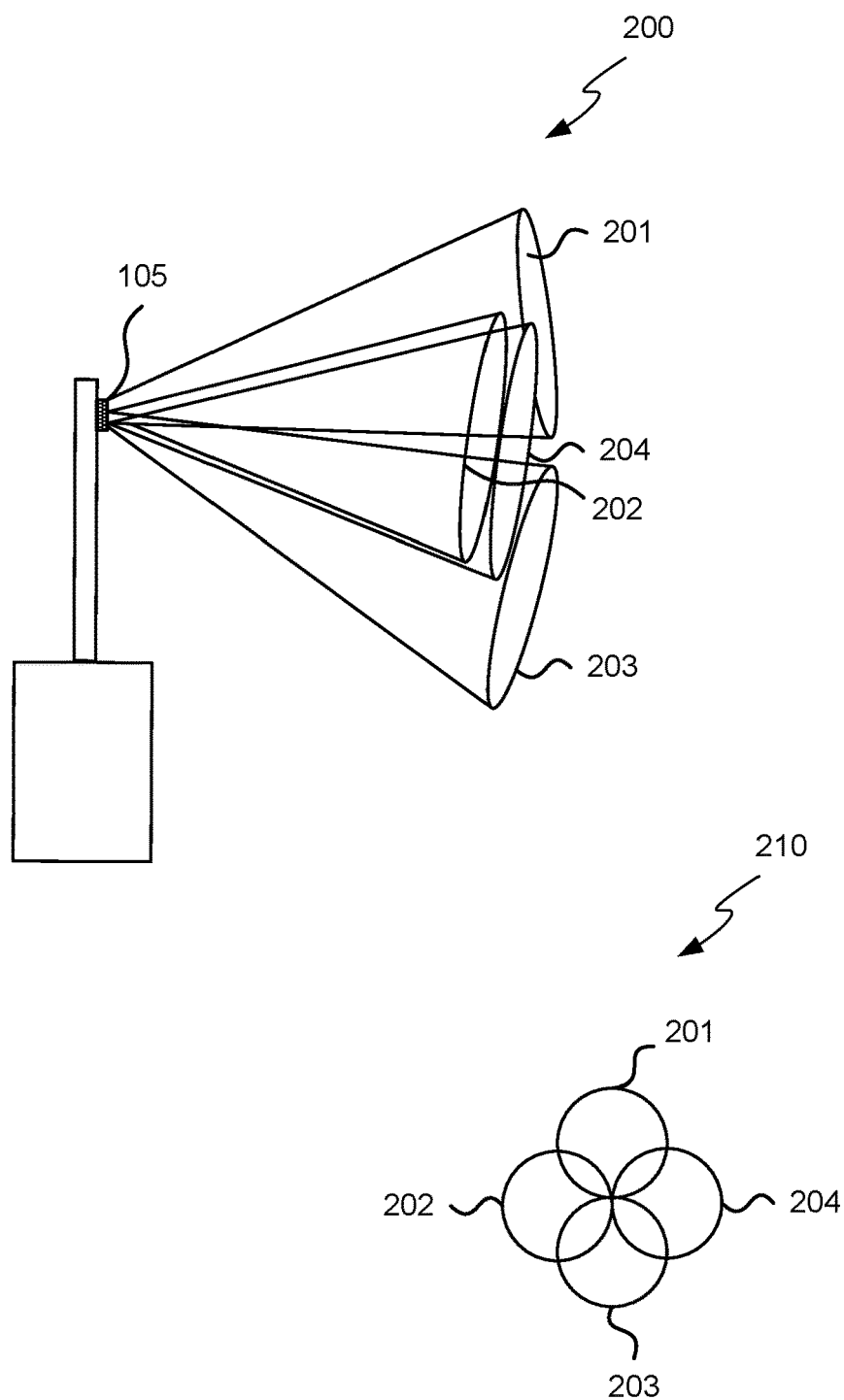
FIG. 2 is a graphical representation of the fields of view of the thermopiles in the system of FIG. 1.

FIG. 1 is a schematic diagram of a system 100 configured to detect the presence and location of a human. The system 100 comprises a plurality of thermopiles 101-104 (e.g. four thermopiles or more than four thermopiles) which may be separate devices or they may be part of one or more thermopile sensor arrays 105 that each comprise a plurality of sensitive areas that independently detect the coming infrared radiation. Each of the plurality of thermopiles 101-104 has a different (i.e. non-identical) field of view and this is represented graphically in FIG. 2. The first diagram 200 in FIG. 2 is a perspective view of the different fields of view 201-204 which may be partially overlapping, e.g. as shown in the cross-section view 210 in FIG. 2. In the example shown in FIG. 2, each field of view of one of the plurality of thermopiles overlaps with the field of view of two other thermopiles from the plurality of thermopiles. In other examples, however, each field of view of one of the plurality of thermopiles may overlap with the field of view of at least one other thermopile from the plurality of thermopiles and in some examples each field of view of one of the plurality of thermopiles may overlap with the field of view of all of the other thermopiles from the plurality of thermopiles. In various examples, the plurality of thermopiles may be arranged in a line such that the field of view of one thermopile partially overlaps the field of view of one or two adjacent thermopiles.

Figure 3:
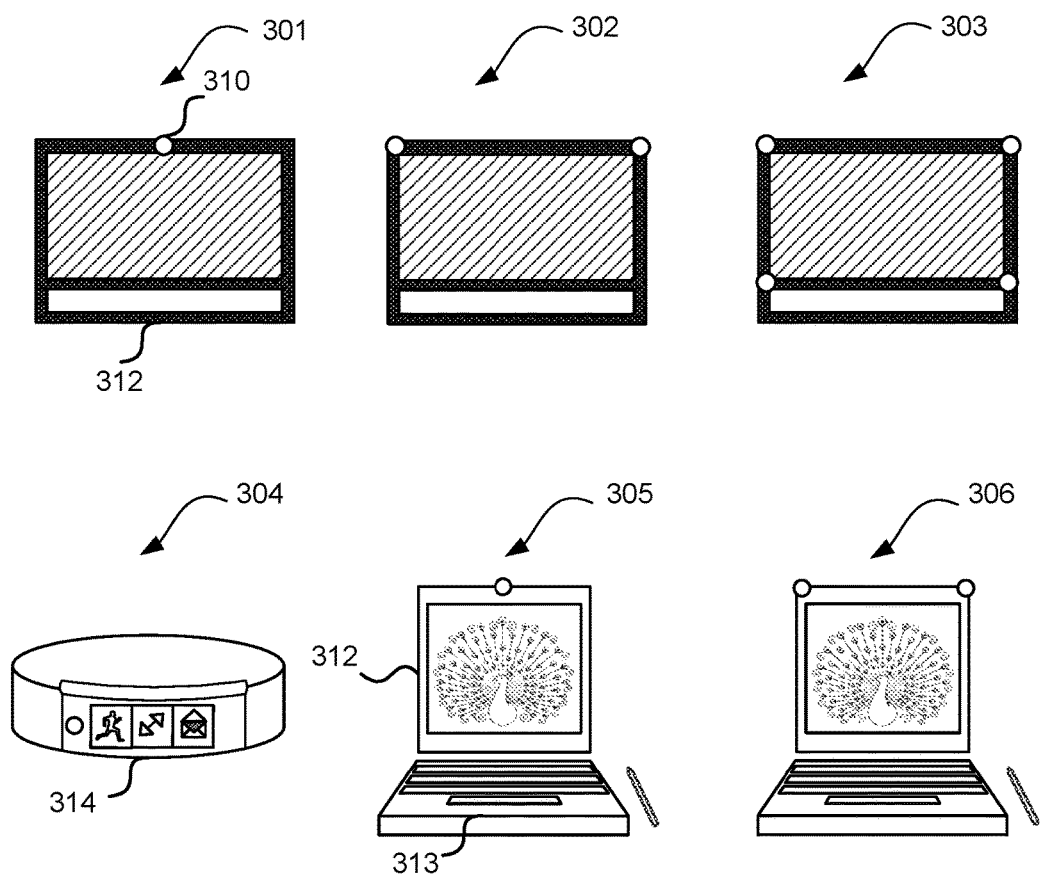
FIG. 3 shows various examples of the positioning of thermopiles on devices.

The sensor data from the plurality of thermopiles 101-104 is received by a location detection module 106 which may be implemented in a computing device which also comprises the thermopiles 101-104 or may be implemented in a computing device which is connected to the thermopiles 101-104 (e.g. the plurality of thermopiles may be integrated into or mounted on a display device which is connected to the computing device). FIG. 3 shows various example devices 301-306 and the positions of thermopile devices 310 on those devices. In the examples shown in FIG. 3, the thermopile devices 310 (as indicated by circles in FIG. 3) may be thermopile sensor arrays 105 which comprise a plurality of thermopiles with different fields of view. Alternatively, in the examples showing a plurality of thermopile devices 310 (the example devices 302, 303 and 306), the thermopile devices 310 may each be single thermopiles, such that the arrangement of thermopile devices 310 comprises a plurality of thermopiles with different fields of view.

In the first three of the example devices 301-303 in FIG. 3 and the last two of the example devices 305-306, the thermopile devices 310 are located in/on a display device 312. Such a display device 312 may for example be a display screen connected to a desktop computer, a display with an integrated computer, a television, part of a laptop computer or tablet computing device with detachable keyboard 313 etc. In such examples, the location of a human that is determined by the location detection module 106 using data from the thermopile devices 310 (using the methods described herein) may be used to control the operation of the display device 312. For example the determined location may be used to control when the display device 312 is switched on and off and/or to control what content is displayed or the way that content is displayed (e.g. by automatically changing the font size of text displayed on the display device 312 dependent upon the determined location). In other examples, such as in the fourth example 304 in FIG. 3, the thermopile devices 310 may be located in/on a wearable device 314 and as described above, the small size and low power consumption makes the thermopile a suitable sensor for small battery powered computing devices such as wearable devices. In other examples, the thermopile devices 310 may be located on other portable computing devices such as a smartphone. In various examples the thermopile devices 310 may be implemented in a device which does not comprise a display (e.g. a voice assistant device) and in various examples this device which incorporates the thermopiles and does not comprise a display may be an accessory device (which may also be referred to as a peripheral device) for a computing device (e.g. an accessory device for a games console).

Although not shown in FIG. 3, in various examples thermopile devices may be integrated into (or placed on) the back of the device (e.g. the back of the display device 312) to provide a 360° field of view.

The location detection module 106 may be implemented in software and/or hardware.

The system 100 further comprises a forward model 110 and stored background values 108 for each field of view. Either or both of the forward model 110 and the stored background values 108 may be considered to be part of the location detection module 106 or may be separate but accessible by the location detection module 106 (e.g. they may be implemented in the same computing device as the location detection module 106 and optionally the plurality of thermopiles 101-104). In various examples, the forward model 110 may be implemented as a lookup table (LUT) and may be implemented in hardware.

Figure 4:
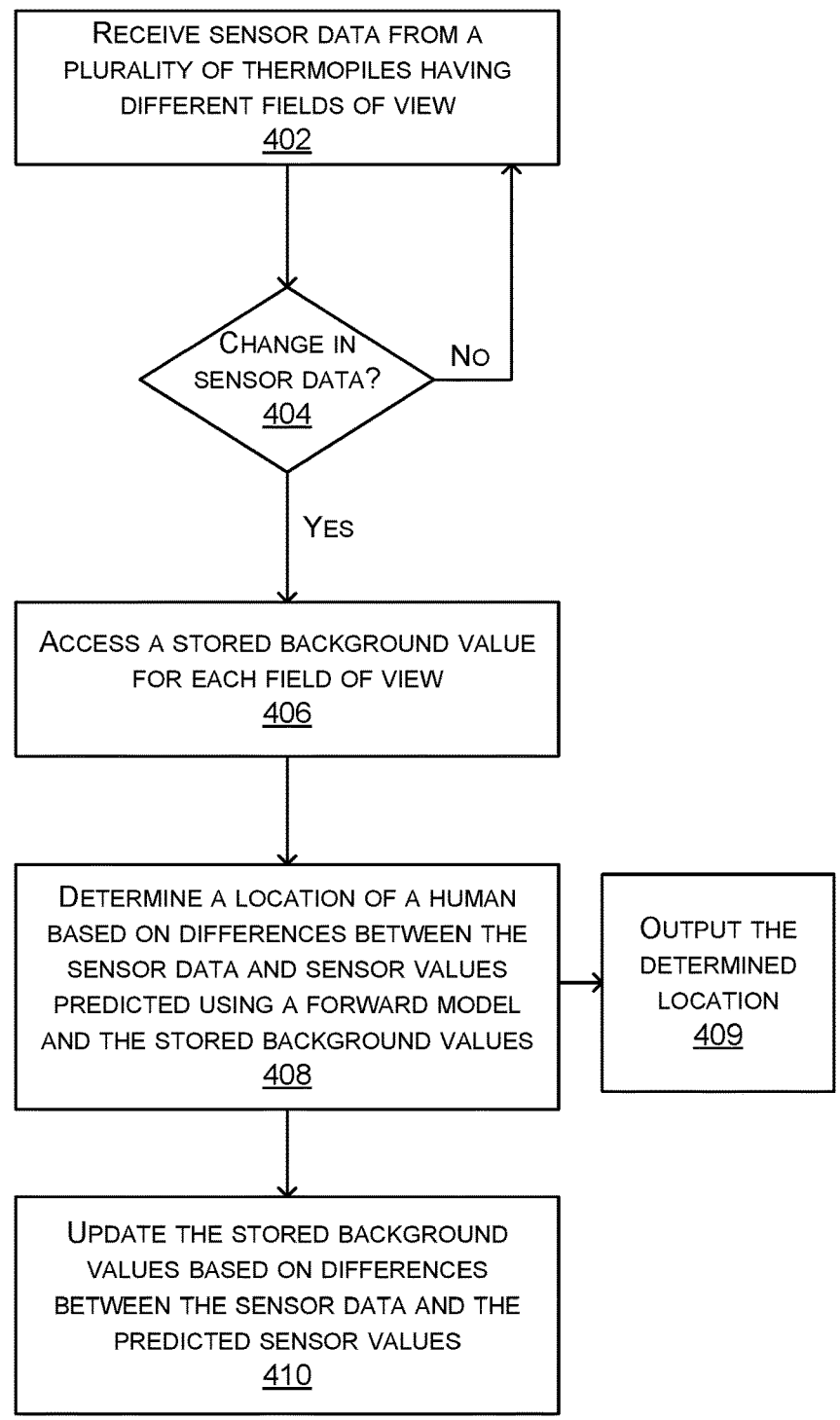
FIG. 4 is a flow diagram of an example method of operation of the location detection module in the system of FIG. 1.

FIG. 4 is a flow diagram of an example method of operation of the location detection module 106. As shown in FIG. 4, the location detection module 106 receives sensor data from a plurality of thermopiles 101-104 having different fields of view (block 402). This sensor data is analyzed and in response to detecting a change in the sensor data ('Yes' in block 404), a stored background value for each field of view is accessed (block 406). The stored background values 108 (as accessed in block 406) are then used along with the forward model 110 to determine the most likely location of a human (block 408) and this location is output by the location detection module (block 409). This determination (in block 408) is made based on differences between the sensor data and sensor values predicted using the forward model and the stored background values for each field of view and this is described in more detail below. Having determined the most likely location of a human (in block 408, e.g. in terms of an angle and optionally a distance), any difference between the predicted sensor values (from the forward model with a human at the determined location) and the received (i.e. actual) sensor data may be used to update the stored background values for one or more of the fields of view (block 410), as described in more detail below.

The forward model 110 is a function of the position of a person (e.g. their angular position relative to the thermopile and their distance from a point of reference defined with respect to the thermopiles, which may, for example, be the position of a thermopile sensor array) and optionally additional parameters, such as their height. The forward model 110 predicts sensor values when a person is located at different locations using analytical forward modeling of the thermopile's field of view. In various examples the person may be represented (in the model) as a cylinder emitting infrared heat; however, more complex representations may alternatively be used. The forward model 110 that is used may comprise a lookup table of predicted sensor values which have been previously calculated (e.g. a table comprising predicted sensor values for a plurality of different positions of a human) or alternatively the forward model 110 may be used to calculate predicted sensor values on the fly (e.g. as part of block 408) using one or more parameters which have been previously determined through training of the model.

Figure 6:
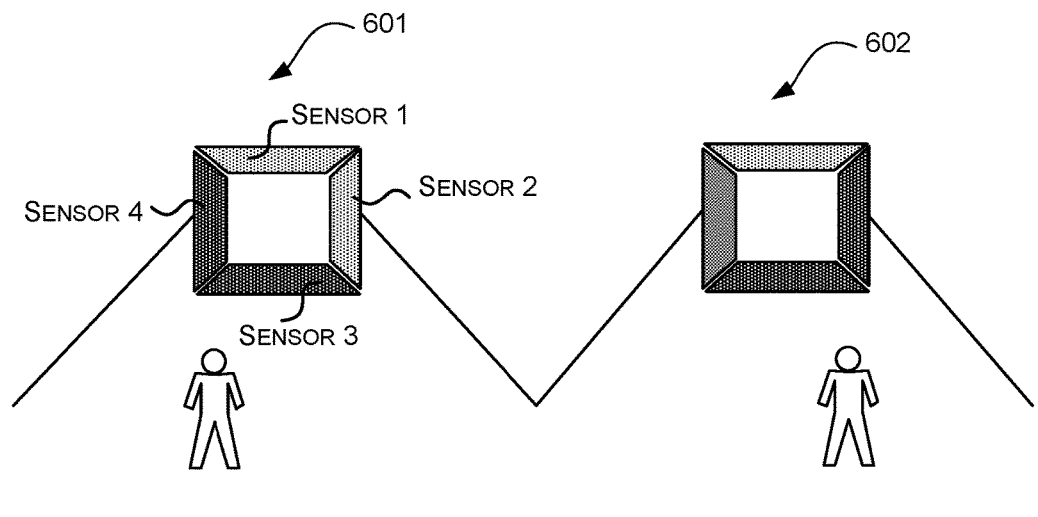
FIG. 6 shows example sensor data for different positions of a human relative to a plurality of thermopiles.
Figure 6:
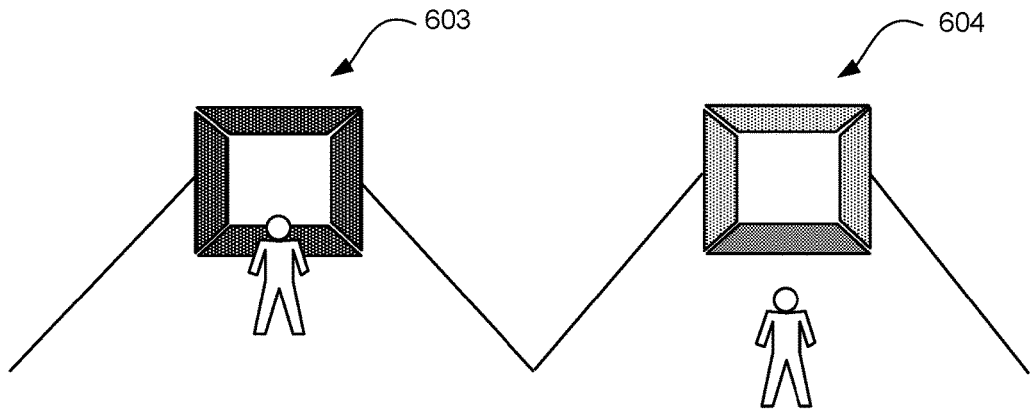

Examples of how the sensor values for the different thermopiles vary for different positions of a human (with respect to the thermopiles) are shown graphically in FIG. 6. FIG. 6 shows four different scenarios 601-604 along with the corresponding sensor data (e.g., the amount of infrared radiation received by each sensor) for the four sensors 1-4 in each scenario.

Where a lookup table is used, the stored sensor values may only relate to the foreground contribution to the predicted value and so the values obtained from the lookup table may be combined with the current stored background values for each field of view (as accessed in block 406) to generate predicted values which are compared with the actual sensor data (in block 408). In other examples, the lookup table may provide data in terms of a contribution or coverage value which defines how the background and foreground values are combined to generate a predicted value. For example, if the stored background value for an $i^{th}$ field of view is denoted $BG_i$, the foreground contribution of a human has a maximum value of FG and the effect of the foreground contribution of the human at an angular position $\propto$ on the $i^{th}$ field of view is $C_\propto^i$, then the lookup table may store a plurality of values of $C_\propto^i$ for the different values of $i$ and $\propto$. The predicted sensor values may then be calculated (in block 408) for different angular positions $\propto$ using:

$$SV_\propto^i = (1-C_\propto^i)BG_i + C_\propto^i FG \qquad (1)$$

And the most likely angular position may be determined by minimizing the difference between the measured sensor values and the predicted sensor values for each of the fields of view (in block 408).

The minimizing (or reducing) of the difference between the measured sensor values and the predicted sensor values for each of the fields of view (in block 408) may be performed using any suitable search technique, such as uniform sampling, brute force or gradient descent (e.g. starting from a last known position of a human and then moving away from this position gradually in order to reduce the difference between the measured sensor values and the predicted sensor values for all of the fields of view). When performing the minimization (or reduction) the differences between the measured sensor value and the predicted sensor values for each of the fields of view may be combined in some way, e.g. using root mean square difference.

In various examples, other sensor inputs to the location detection module 106 may be used to influence the search. For example if a user is typing on a keyboard connected to the computing device, the search may initially focus on a position directly in front of the keyboard, or if a user is only pressing the arrow keys, the search may initially focus on a position on the same side as the arrow keys on a keyboard. Depending upon the particular implementation, the search may include certain assumptions, such as the distance between the human and the point of reference defined by the thermopile positions being no smaller than a minimum separation (e.g. based on a standard position of a user when reading a display).

In various examples time based filtering may be used to influence the search. For example, if a human is determined using the methods described herein to be at a first location, L1, when the method is next performed, the search may be constrained to consider, at least initially, locations which are proximate to L1 (e.g. where the proximity is determined based on human motion characteristics). In this way a human is assumed to move smoothly through the field of view and not jump large distances in short periods of time. In various examples, a particle filter may be used such that the location detection module 106 may track multiple hypotheses for the possible locations of a human (e.g. the method may determine, in block 408, that the three most probably locations of a human are A, B and C) and report the most probable location (e.g. location A, in block 408). In the event that there is evidence that the hypothesis that was followed is wrong (e.g. because a new identified location of a human, D, is too far from the previously reported location A of a human), the location detection module 106 can then switch to one of the other tracked hypotheses which is supported by the new evidence (e.g. if location D is close to location B).

In various examples the forward model 110 may use polar coordinates and in various examples the location of the human may be determined in terms of both an angular position $\propto$ and a distance d. In such examples, the lookup table (where used) may store a plurality of contribution values $C_{\propto,d}^{i}$ for different angular positions and different distances and the method may operate in the same way as described above but with an additional degree of freedom in the search space, i.e. such that equation (1) becomes:

$$SV_{\propto,d}^{i}=(1-C_{\propto,d}^{i})BG_i+C_{\propto,d}^{i}FG \qquad (2)$$

In other examples where the forward model is used in real-time to calculate predicted sensor values (in block 408), the stored background values 108 for each of the fields of view may be input into the forward model 110. In various examples one or more adaptive parameters may also be fed into the forward model 110, such as the angular position of a laptop computer lid (e.g. as detected by an angular sensor in the lid and/or body of the device) or a current location and viewing angle of a device.

Figure 5:
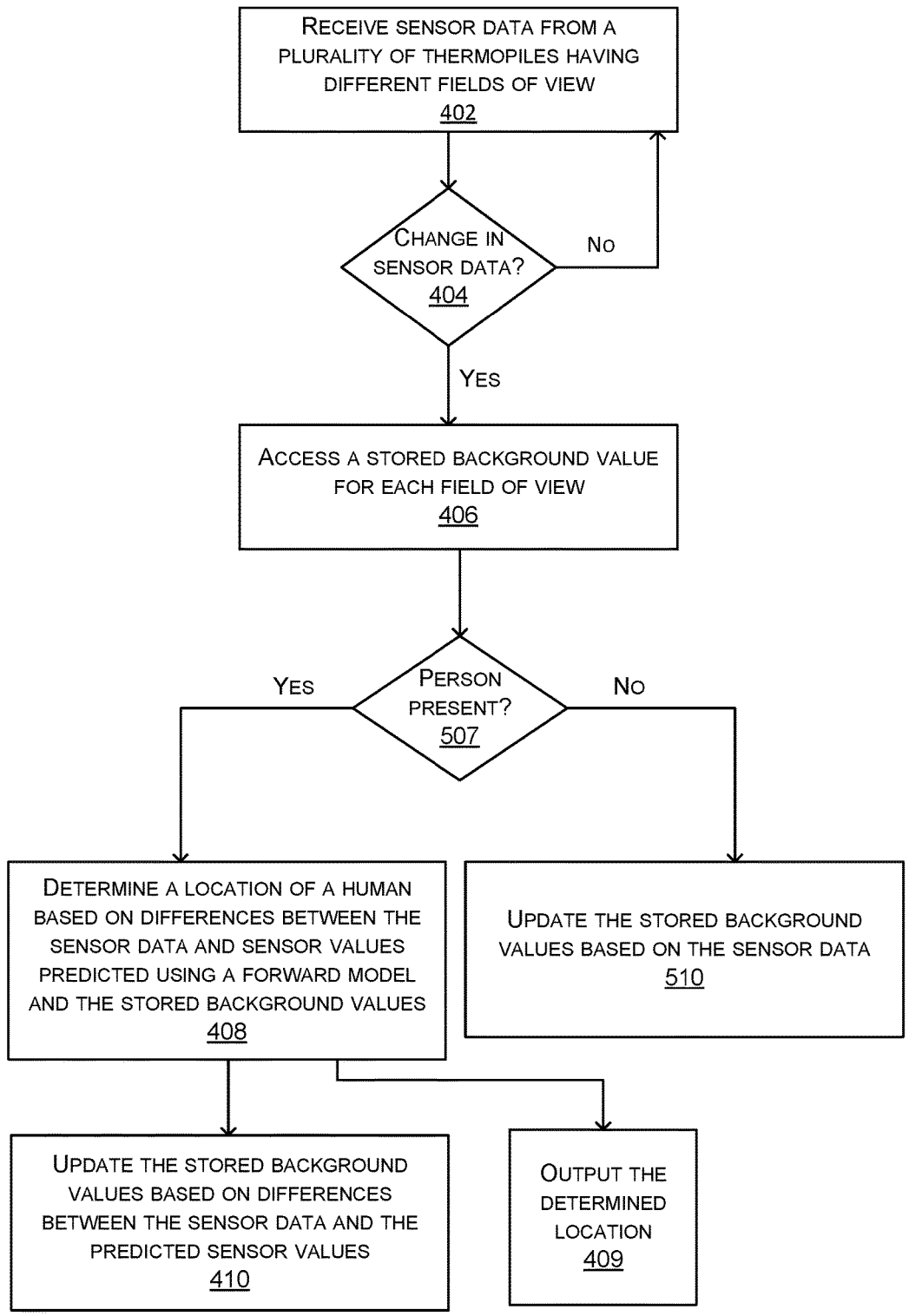
FIG. 5 is a flow diagram of another example method of operation of the location detection module in the system of FIG. 1.

It will be appreciated that the location that is determined using the forward model (in block 408) may be a location of a human (e.g. as defined by an angle and optionally a distance) or an indication that no human is present within the fields of view of any of the plurality of thermopiles. In a variation of the method, as shown in FIG. 5, the location may only be determined if it determined that a user is present ('Yes' in block 507); however, the stored background values may be updated (in block 410 or 510) in both situations, i.e. irrespective of whether a human is present, although different rules may be used to perform the updating of the stored background values dependent upon whether a human is present ('Yes' in block 507 if FIG. 5 or a location of a human is identified in block 408 of FIG. 4) or not ('No' in block 507 if FIG. 5 or no location of a human is identified in block 408 of FIG. 4).

The presence detection (in block 507) may be performed using heuristics (i.e. subtracting the stored background value from the sensor data for each thermopile and determining if the resulting values for one or more of the thermopiles exceeds a threshold value) or by applying a binary classifier to the raw sensor data that is trained on a ground truth of sensor values.

The differences between the sensor data and the predicted sensor values for different possible locations of a human (as determined in block 408) provide a probability map for the location of a human, with the determined location being the location with the smallest difference and hence highest probability of being the correct location for the human. In various examples, an additional test may be performed when determining the location and if the difference between the sensor data and the closest predicted sensor values exceeds a pre-defined threshold, additional measures may be triggered to assist in determining the location of the human. For example, if the threshold is exceeded, a camera may be switched on and image processing performed on one or more images captured using the camera to assist in locating a human. Alternatively, if the threshold is exceeded, an error may be triggered to indicate that the location of a human (or confirmation that no human is present) cannot be determined with sufficient confidence.

In the event that a location of a person is identified (in block 408), the stored background values 108 are updated based on differences between the sensor data and the predicted sensor values for a human at the determined location (block 410). For example, the background values may be updated using equation (1) above with values of $C_{\propto}^{i}$ (or equation (2) with values $C_{\propto,d}^{i}$) corresponding to the determined location. Using these values, the stored background values $BG_i$ are modified such that the differences between predicted sensor values and the actual sensor values are reduced or eliminated.

In the event that a location of a person is not identified (in block 408 of FIG. 4) or a person is not identified as being present ('No' in block 507 of FIG. 5), the stored background values 108 may still be updated (in blocks 410 and 510) based on differences between the sensor data and the predicted sensor values (where the predicted sensor values in this situation may be equal to the stored background values). In addition, or instead, the stored background values 108 may be updated (in blocks 410 and 510) based on another parameter such as a timer or an error correction value (or signal).

In various examples, in the event that a location of a person is not identified (in block 408 of FIG. 4) or a person is not identified as being present ('No' in block 507 of FIG. 5), the location detection module 106 may compare the differences between the sensor data and the predicted sensor values (where the predicted values may equal the stored background values 108) either at one point in time or over a period of time and if the differences are the same for all fields of view (e.g. to a predefined accuracy), then the stored background values 108 may be updated to match the sensor data (in block 510). In various examples this may be implemented only if it results in a decrease in the stored background values 108 and in other examples, the stored background values 108 may be reset to match the sensor data irrespective of whether it results in an increase or a decrease in the stored background values 108. This updating of the stored background values 108 in the absence of a human, but where the sensor data for all of the fields of view are correlated, provides correction for drift of the sensor performance over time.

In various examples the stored background values 108 may be updated in the absence of a human where there is no correlation between the differences, but where the rate of change that is detected is very small (i.e. the sensor values are changing very slowly). This updating of the stored background values 108 in the absence of a human accommodates slow local changes in the background temperature (e.g. a radiator emitting heat in the field of view of only one sensor), which may not affect all the thermopiles in the same way.

In various examples a timer may be used to reset the stored background values 108 to match the sensor data in the event that no human has been detected (in either block 408 or block 507) for more than a pre-defined period of time. This updating of the stored background values 108 in the absence of a human accommodates local changes in the background temperature which may not affect all the thermopiles in the same way (e.g. a radiator emitting heat in the field of view of only one sensor). Additionally this updating of the stored background values 108 in the absence of a human compensates for the fact that the background values, which are an estimate of the background infrared level, will inherently become less accurate over time. In various examples the timer may be used in combination with other sensors such as a motion sensor located in or on the same device as the plurality of thermopiles. In such an example, if the motion sensor does not detect any motion in a pre-defined period of time (as determined by the timer), the stored background values 108 may be reset to match the sensor data. In various examples motion sensor data may in addition or instead be used to control the operation of the location detection module 106 in other ways. For example, the location determination may only be performed (e.g. using the method of FIG. 4 or 5) when the device comprising the plurality of thermopiles is not moving (e.g. as determined based on data from the motion sensors).

Instead of, or in addition to, using a timer (as described above), an error correction value may be stored for each of the plurality of thermopiles and the error correction values may be reset to be equal to the stored background values 108 each time the stored background values are updated (in blocks 410 and 510). After each resetting of the error correction values, the error correction values for each thermopile may then be increased at a pre-defined rate (e.g. such that the values increment slowly) or dependent upon the variation observed in the sensor data (e.g. in correspondence to features extracted from sensor data for two or more of the plurality of thermopiles) and if the error correction value for any of the plurality of thermopiles increases to a value which equals the sensor data, then the stored background value 108 and the error correction value for that thermopile may be updated to be equal to the sensor data. In various examples the error correction values may operate independently for the different thermopiles but in other examples they may not operate independently and instead the stored background values 108 and error correction values may be reset dependent upon pre-defined criteria being met for all of the plurality of thermopiles (e.g. when the error correction value for all of the plurality of thermopiles increases to a value which equals the sensor data).

In various examples, the range at which the error correction values are incremented may be varied based on certain parameters. For example, if the thermopiles are in/on a portable computing devices and a motion sensor in the computing device detects motion, then the error correction values may be increased faster; however, the stored background values may not be reset to be equal to the sensor data until the detected motion has stopped. This has the effect of resetting the stored background values more quickly in the event of motion of the computing device (i.e. in the event of motion of the device the stored background values are decayed more quickly).

In the methods described above and shown in FIGS. 4 and 5, the drift correction is only performed in the absence of a human (in block 510). In other examples, however, correction for any drift may additionally be performed when a human is present and this drift correction may be performed before or after the location of human has been determined. In other examples drift compensation may not be required (e.g. because the thermopiles are sufficiently stable that any drift does not affect the determination of a location) or drift compensation may be executed internally in the thermopile or associated circuitry (e.g. before or after the values are digitized) and this may be performed based, for example, on the thermopile's internal temperature.

Figure 9:
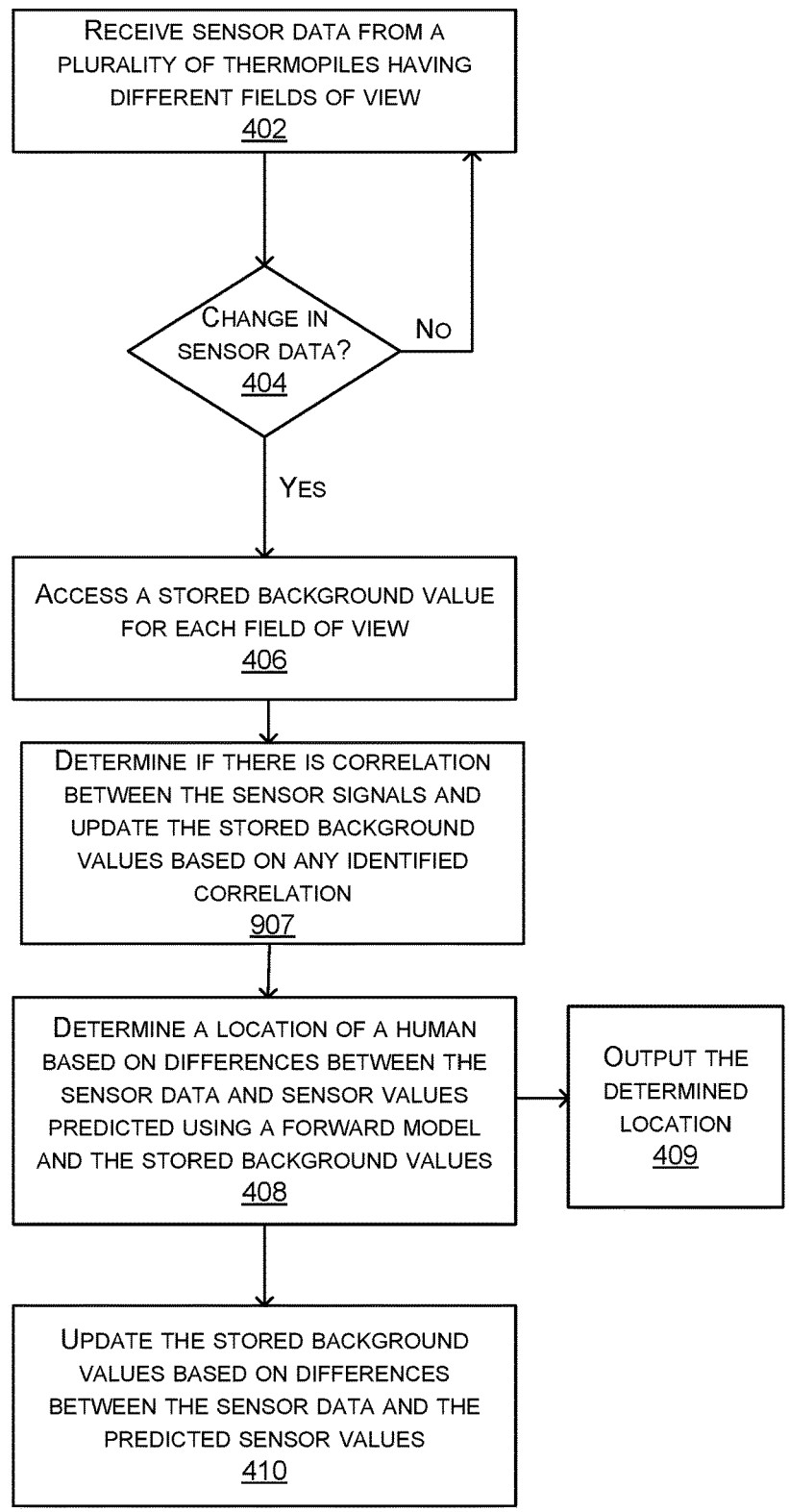
FIG. 9 is a flow diagram of a further example method of operation of the location detection module in the system of FIG. 1.

FIG. 9 shows a flow diagram of an example method of operation of a location detection module 106 which is a variation on that shown in FIG. 4 and described above. The example includes the additional stage of determining if there is any correlation between the sensor data for each of the fields of view and if a correlation is identified, the stored background values are updated based on this correlation (block 907). As described above, this enables any drift in the sensor performance to be compensated for prior to determining the location of a human (in block 408).

Figure 10:
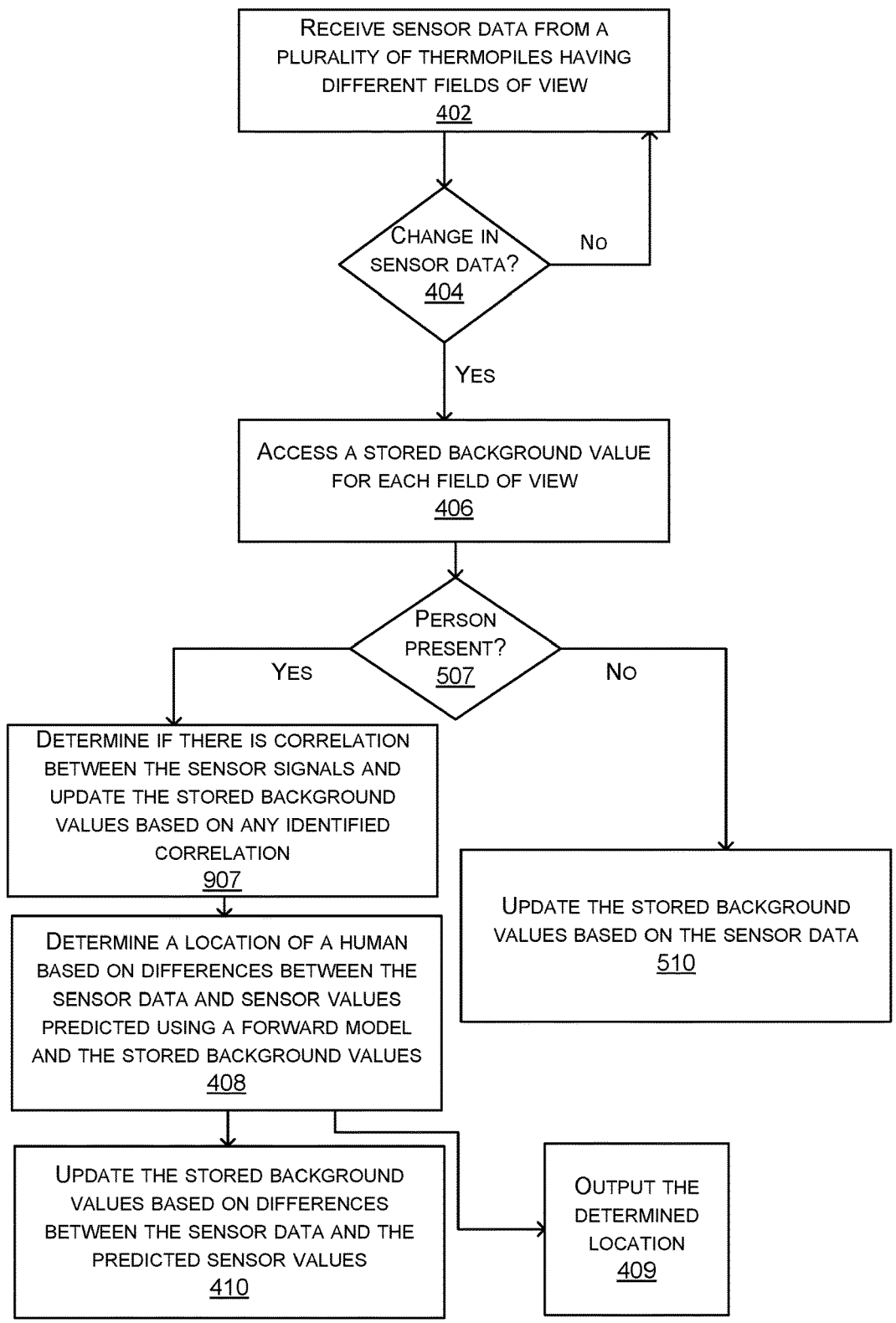
FIG. 10 is a flow diagram of yet another example method of operation of the location detection module in the system of FIG. 1.

FIG. 10 shows a flow diagram of an example method of operation of a location detection module 106 which is a variation on that shown in FIG. 5 and described above. In a similar manner to FIG. 9, the method shown in FIG. 10 includes the additional stage of determining if there is any correlation between the sensor data for each of the fields of view and if a correlation is identified, the stored background values are updated based on this correlation (block 907). As described above, this enables any drift in the sensor performance to be compensated for prior to determining the location of a human (in block 408).

Figure 7:
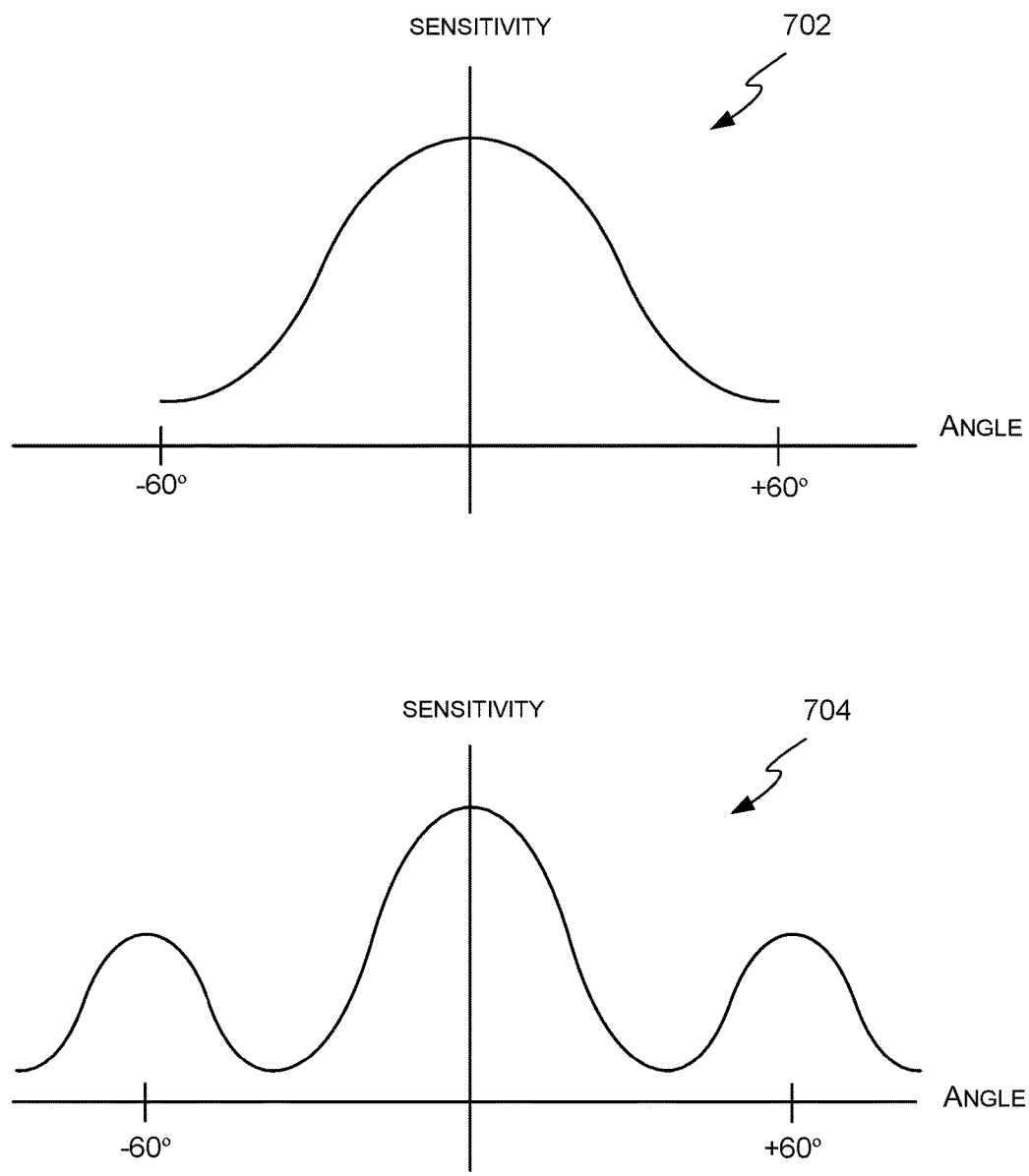
FIG. 7 shows example response curves for a thermopile with and without a lens.

The field of view of a thermopile 101-104 may be symmetric, as shown in the first sensitivity graph 702 shown in FIG. 7. In other examples, however, the field of view may not be completely symmetrical (e.g. as a consequence of a non-symmetric design of the thermopile). In various examples, the system 100 may comprise one or more lenses, each of which may be positioned in front of one of the plurality of thermopiles 101-104. By using a lens, the shape of the field of view can be modified (e.g. the angle of the field of view may be reduced) and this may, for example, be used to increase the sensing range and/or accuracy of location determination. The second sensitivity graph 704 shows such an example which may provide an increased sensing range. In various examples a Fresnel lens (e.g. compound lens comprised of many Fresnel elements) may be used which has more dead zones (i.e. zones of low sensitivity) between peaks of higher sensitivity than are shown in the second sensitivity graph 704 in FIG. 7.

Having determined the location of a human using the methods described above, this information may be used in many different ways. For example, having determined the location of a human, this may be used to turn a computing device or part of the hardware (e.g. the display) and/or software (e.g. the voice recognition software) of the computing device, on and off. This improves the efficiency of the computing device by reducing the power consumption when no human is in the vicinity of the computing device. In another example, the computing device may change its operation based on the determined location (e.g. by changing the content displayed or the way the content is displayed, dependent upon the determined location).

Figure 8:
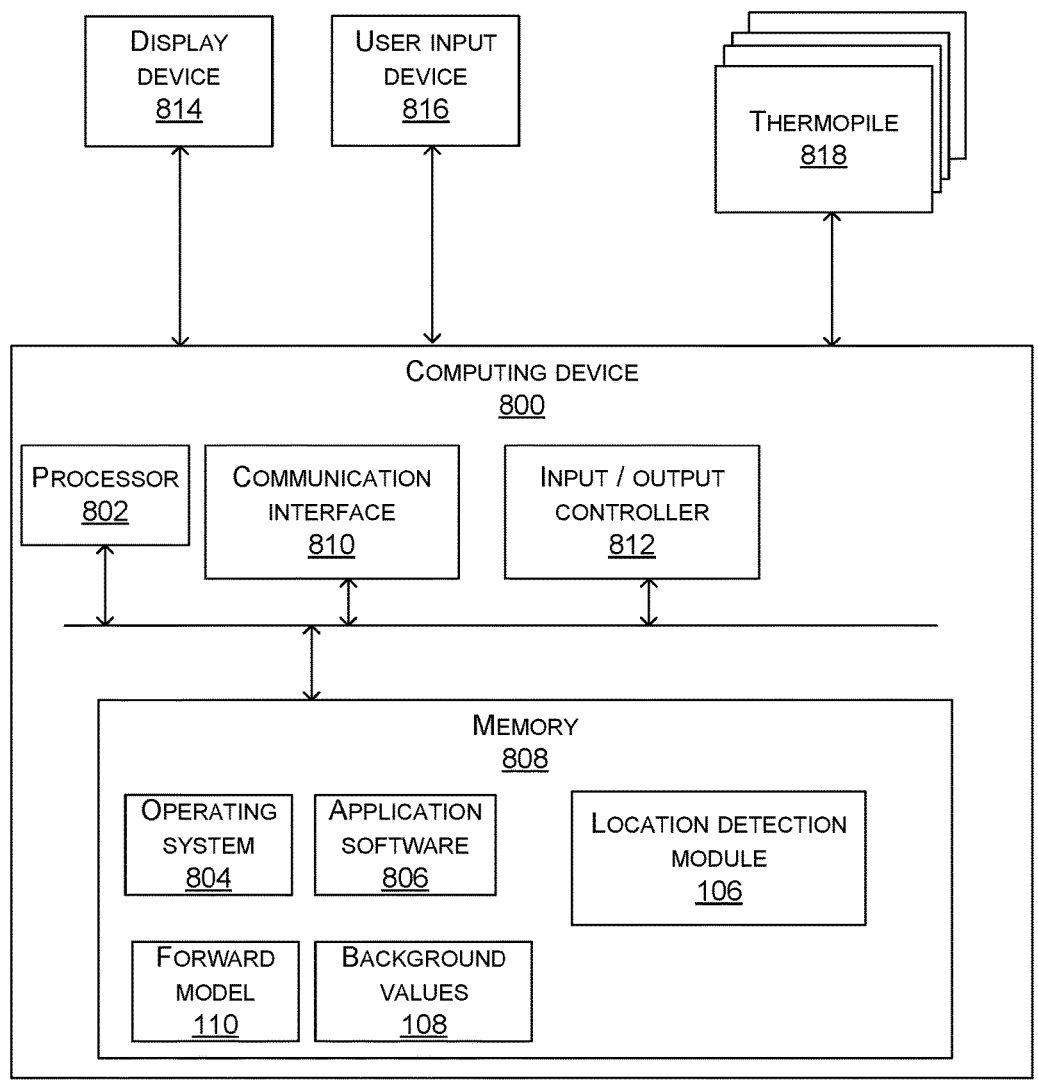
FIG. 8 illustrates an exemplary computing-based device in which embodiments of the methods of any of FIG. 4, 5, 9 or 10 are implemented.

FIG. 8 illustrates various components of an exemplary computing-based device 800 which are implemented as any form of a computing and/or electronic device, and in which embodiments of the methods described above are implemented in some examples.

Computing-based device 800 comprises one or more processors 802 which are microprocessors, controllers or any other suitable type of processors for processing computer executable instructions to control the operation of the device in order to perform the methods described above. In some examples, for example where a system on a chip architecture is used, the processors 802 include one or more fixed function blocks (also referred to as accelerators) which implement a part of the method of determining the location of a human in hardware (rather than software or firmware). Platform software comprising an operating system 804 or any other suitable platform software may be provided at the computing-based device to enable application software 806 and the location detection module 106 to be executed on the device.

Alternatively, or in addition, the functionality of the location detection module 106 described herein may be performed, at least in part, by one or more hardware logic components. For example, and without limitation, illustrative types of hardware logic components that are optionally used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), Graphics Processing Units (GPUs).

The computer executable instructions (e.g. for the location detection module 106 when implemented in software) are provided using any computer-readable media that is accessible by computing based device 800. Computer-readable media includes, for example, computer storage media such as memory 808 and communications media. Computer storage media, such as memory 808, includes volatile and non-volatile, removable and non-removable media implemented in any method or technology for storage of information such as computer readable instructions, data structures, program modules or the like. Computer storage media includes, but is not limited to, random access memory (RAM), read only memory (ROM), erasable programmable read only memory (EPROM), electronic erasable programmable read only memory (EEPROM), flash memory or other memory technology, compact disc read only memory (CD-ROM), digital versatile disks (DVD) or other optical storage, magnetic cassettes, magnetic tape, magnetic disk storage or other magnetic storage devices, or any other non-transmission medium that is used to store information for access by a computing device. In contrast, communication media embody computer readable instructions, data structures, program modules, or the like in a modulated data signal, such as a carrier wave, or other transport mechanism. As defined herein, computer storage media does not include communication media. Therefore, a computer storage medium should not be interpreted to be a propagating signal per se. Although the computer storage media (memory 808) is shown within the computing-based device 800 it will be appreciated that the storage is, in some examples, distributed or located remotely and accessed via a network or other communication link (e.g. using communication interface 810).

The computing-based device 800 may also comprises an input/output controller 812 arranged to output display information to a display device 814 which may be separate from or integral to the computing-based device 800. The display information may provide a graphical user interface. The input/output controller 812 may also be arranged to receive and process input from one or more devices, such as a user input device 816 (e.g. a mouse, keyboard, camera, microphone or other sensor). In some examples the user input device 816 detects voice input, user gestures or other user actions and provides a natural user interface (NUI). This user input may be used to control application software 806 running on the computing based device 800 and as described above, in various examples, the user input may be used in location determination by the location detection module 106. In an embodiment the display device 814 also acts as the user input device 816 if it is a touch sensitive display device.

The input/output controller 812 or the communication interface 810 may also receive sensor data from a plurality of thermopiles 818 having different fields of view. The thermopiles 818 may be separate from or integral to the display device 814, the user input device 816 and/or the computing device 800.

The input/output controller 812 may also output data to devices other than the display device, e.g. a locally connected printing device (not shown in FIG. 8).

Any of the input/output controller 812, display device 814 and the user input device 816 may comprise NUI technology which enables a user to interact with the computing-based device in a natural manner, free from artificial constraints imposed by input devices such as mice, keyboards, remote controls and the like. Examples of NUI technology that are provided in some examples include but are not limited to those relying on voice and/or speech recognition, touch and/or stylus recognition (touch sensitive displays), gesture recognition both on screen and adjacent to the screen, air gestures, head and eye tracking, voice and speech, vision, touch, gestures, and machine intelligence. Other examples of NUI technology that are used in some examples include intention and goal understanding systems, motion gesture detection systems using depth cameras (such as stereoscopic camera systems, infrared camera systems, red green blue (RGB) camera systems and combinations of these), motion gesture detection using accelerometers/gyroscopes, facial recognition, three dimensional (3D) displays, head, eye and gaze tracking, immersive augmented reality and virtual reality systems and technologies for sensing brain activity using electric field sensing electrodes (electro encephalogram (EEG) and related methods).

In the examples described above, the angular position and optionally location of a human may be identified using a plurality of thermopiles with different fields of view. If more than four thermopiles are used (such that there are more than four different fields of view), additional parameters relating to the human may also be determined using the stored background values 108 and the forward model 110 by including these additional parameters within the forward model 110. For example, the height and/or temperature of the human may additionally be determined. In various examples, through use of more than four thermopiles with different fields of view and a modified forward model 110, the methods described above may be used to determine the location of more than one human within the fields of view of the thermopiles.

The use of a forward model 110 as described above (and in combination with a plurality of thermopiles with different fields of view) to determine the location of a human (relative to the plurality of thermopiles), provides a method which uses less computational power (and hence less energy), and in various examples less memory, space and/or peripherals, than many alternative techniques (e.g. use of neural networks). This makes the method well suited to implementation in devices with limited computational power, such as embedded devices. As described above the methods are also more easily used to evaluate multiple hypotheses (e.g. through particle filtering) on devices with limited computational power.

Although the present examples are described and illustrated herein as being implemented in a computing system as shown in FIG. 1, the system described is provided as an example and not a limitation. As those skilled in the art will appreciate, the present examples are suitable for application in a variety of different types of computing systems. Additionally it will be appreciated that equations (1) and (2) above provide just one example method of calculating the predicted values based on the forward model 110 and stored background values 108. In other examples more complex equations may be used (e.g. surface integrals over the field of view) and as described above, the forward model may use a more complex representation of a human than a cylinder. In addition or instead, the forward model may include one or more additional parameters, for example, any one or more of: height, body temperature, leaning angle, head position, etc.

Although the examples are described above in relation to detecting the location of a human, in other examples the methods may be used to detect the location of other bodies, such as other warm bodies or bodies which have a temperature which is differentiated from the background. For example the methods may be used to detect the location of an animal. The body which is detected (and its location determined) using the methods described herein is a moving body, in that it moves relative to the background, however, at the time that the location is determined using the methods described above the body may not be moving (e.g. a human may be standing or sitting still for a period of time, but will move again at the end of that period of time).

Alternatively or in addition to the other examples described herein, examples include any combination of the features set out below.

A first further example provides a method of detecting presence and location comprising: receiving sensor data from a plurality of thermopiles, each thermopile having a different field of view; in response to detecting a change in the sensor data, accessing stored background values for each field of view, determining a location of a body based on differences between the sensor data and sensor values predicted using a forward model and the stored background values for each field of view; and updating the stored background values based on differences between the sensor data and the predicted sensor values.

The second further example provides a method of detecting human presence and location comprising: receiving sensor data from a plurality of thermopiles, each thermopile having a different field of view; in response to detecting a change in the sensor data, accessing stored background values for each field of view, determining a location of a human body based on differences between the sensor data and sensor values predicted using a forward model and the stored background values for each field of view; and updating the stored background values based on differences between the sensor data and the predicted sensor values.

The first and second further examples may include any combination of one or more of the following features:

- the method may further comprise outputting the determined location;
- the method may further comprise using the determined location to control operation of a device.
- the location may be determined by minimizing the differences between the sensor data and sensor values predicted using the forward model and the stored background values for each field of view.
- the stored background values may be updated by changing the stored background values to reduce the differences between the sensor data and sensor values predicted using the forward model and the stored background values for each field of view for a body at the determined location;
- the stored background values may be updated by changing the stored background values to minimize the differences between the sensor data and sensor values predicted using the forward model and the stored background values for each field of view for a body at the determined location.
- the field of view of one of the plurality of thermopiles may partially overlap the field of view of a different one (or more than one) of the plurality of thermopiles or may partially overlap the field of view of all others of the plurality of thermopiles.
- the location of a body may comprise an angular position of the body relative to the plurality of thermopiles or an indication that no body is present.
- in response to determining that the location comprises an indication that no body is present, updating the stored background values may comprise: determining if there is a correlation between the differences between the sensor data and the predicted sensor values for each of the plurality of thermopiles and in response to identifying a correlation, updating the stored background values to be equal to the sensor data.
- in response to determining that the location comprises an indication that no body is present, updating the stored background values may comprise: in response to determining that no body has been present for more than a predefined period of time, updating the stored background values to be equal to the sensor data.
- the location of a body may further comprise a distance of the body from the plurality of thermopiles.
- the method may further comprise: storing an error correction value for each of the plurality of thermopiles; resetting the error correction values to be equal to the stored background values each time the stored background values are updated; incrementing the error correction values over time and/or in correspondence to features extracted from sensor data for two or more of the plurality of thermopiles; and in response to determining that the error correction value for any of the plurality of thermopiles equals the sensor data for that thermopile, updating the stored background value for the thermopile to be equal to the sensor data for that thermopile.
- the method may further comprise: in response to detecting a change in the sensor data, determining if a body is present; and wherein the method may comprise: in response to determining that a body is present, determining a location of a body based on differences between the sensor data and sensor values predicted using a forward model and the stored background values for each field of view; and updating the stored background values based on differences between the sensor data and the predicted sensor values; and in response to determining that a body is not present, updating the stored background values based on the sensor data.

A third further example provides a system for detecting presence and location comprising: a plurality of thermopiles, each thermopile having a different field of view; a location detection module; a forward model; and a data store arranged to store a background value for each of the plurality of thermopiles, wherein the location detection module is arranged to receive sensor data from the plurality of thermopiles and in response to detecting a change in the sensor data, to access the stored background values for each field of view, to determine a location of a body based on differences between the sensor data and sensor values predicted using the forward model and the stored background values; and to update the stored background values based on differences between the sensor data and the predicted sensor values.

A fourth further example provides a system for detecting human presence and location comprising: a plurality of thermopiles, each thermopile having a different field of view; a location detection module; a forward model; and a data store arranged to store a background value for each of the plurality of thermopiles, wherein the location detection module is arranged to receive sensor data from the plurality of thermopiles and in response to detecting a change in the sensor data, to access the stored background values for each field of view, to determine a location of a human body based on differences between the sensor data and sensor values predicted using the forward model and the stored background values; and to update the stored background values based on differences between the sensor data and the predicted sensor values.

The third and fourth further examples may include any combination of one or more of the following features:
  an output for outputting the determined location.
  the location of a body may be determined by minimizing the differences between the sensor data and sensor values predicted using the forward model and the stored background values for each field of view.
  the stored background values may be updated by changing the stored background values to reduce the differences between the sensor data and sensor values predicted using the forward model and the stored background values for each field of view for a body at the determined location.
  the system may further comprise a motion sensor and wherein the location detection module is further arranged to update the stored background values in response to motion sensor data.
  the system may further comprise a plurality of lenses and wherein the lenses are positioned in front of the plurality of thermopiles.
  the system may further comprise a display device and wherein the plurality of thermopiles are integrated into or mounted on the display device.
  the forward model may comprise a lookup table arranged to store a value for a maximum forward contribution of a body to the sensor values and a plurality of values detailing the effect of the foreground contribution of the body at different locations relative to the plurality of thermopiles.
  the location detection module may be at least partially implemented using hardware logic selected from any one or more of: a field-programmable gate array, a program-specific integrated circuit, a program-specific standard product, a system-on-a-chip, a complex programmable logic device.

A fifth further example comprises a computing device for detecting presence and location comprising: an input for receiving sensor data from a plurality of thermopiles, each thermopile having a different field of view; a processor; and memory configured to store background values for each of the plurality of thermopiles, data defining a forward model and computer executable instructions, which when executed cause the processor, in response to detecting a change in the sensor data, to: access the stored background values for each field of view; determine a location of a body based on differences between the sensor data and sensor values predicted using the forward model and the stored background values; and update the stored background values based on differences between the sensor data and the predicted sensor values.

A sixth further example comprises a computing device for detecting human presence and location comprising: an input for receiving sensor data from a plurality of thermopiles, each thermopile having a different field of view; a processor; and memory configured to store background values for each of the plurality of thermopiles, data defining a forward model and computer executable instructions, which when executed cause the processor, in response to detecting a change in the sensor data, to: access the stored background values for each field of view; determine a location of a human body based on differences between the sensor data and sensor values predicted using the forward model and the stored background values; and update the stored background values based on differences between the sensor data and the predicted sensor values.

The term 'computer' or 'computing-based device' is used herein to refer to any device with processing capability such that it executes instructions. Those skilled in the art will realize that such processing capabilities are incorporated into many different devices and therefore the terms 'computer' and 'computing-based device' each include personal computers (PCs), servers, mobile telephones (including smart phones), tablet computers, set-top boxes, media players, games consoles, personal digital assistants, wearable computers, and many other devices.

The methods described herein are performed, in some examples, by software in machine readable form on a tangible storage medium e.g. in the form of a computer program comprising computer program code means adapted to perform all the operations of one or more of the methods described herein when the program is run on a computer and where the computer program may be embodied on a computer readable medium. The software is suitable for execution on a parallel processor or a serial processor such that the method operations may be carried out in any suitable order, or simultaneously.

This acknowledges that software is a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language)

software, as is used for designing silicon chips, or for configuring universal programmable chips, to carry out desired functions.

Those skilled in the art will realize that storage devices utilized to store program instructions are optionally distributed across a network. For example, a remote computer is able to store an example of the process described as software. A local or terminal computer is able to access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a digital signal processor (DSP), programmable logic array, or the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The operations of the methods described herein may be carried out in any suitable order, or simultaneously where appropriate. Additionally, individual blocks may be deleted from any of the methods without departing from the scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this specification.

The invention claimed is:

1. A method of detecting presence and location of a body using a mobile computing device, the method comprising:
   receiving sensor data from a plurality of thermopiles coupled to the mobile device, each thermopile having a different field of view;
   in response to detecting a change in the sensor data, accessing stored background values for each field of view;
   determining, using a forward model, sensor values corresponding to locations of the body by applying the sensor data to a lookup table within the forward model;
   determining a location of the body based on differences between sensor values within the sensor data and the determined sensor values from the forward model, and the differences between the sensor data and the stored background values for each field of view; and
   updating the stored background values based on differences between the sensor data and the determined sensor values.

2. The method according to claim 1, wherein the location is determined by reducing the differences between the sensor data and sensor values predicted using the forward model and the stored background values for each field of view.

3. The method according to claim 1, wherein the stored background values are updated by changing the stored background values to reduce the differences between the sensor data and sensor values predicted using the forward model and the stored background values for each field of view for the body at the determined location.

4. The method according to claim 3, wherein the stored background values are updated by changing the stored background values to reduce the differences between the sensor data and sensor values predicted using the forward model and the stored background values for each field of view for the body at the determined location.

5. The method according to claim 1, wherein the field of view of one of the plurality of thermopiles partially overlaps the field of view of a different one of the plurality of thermopiles.

6. The method according to claim 1, wherein the location of the body comprises an angular position of the body relative to the plurality of thermopiles or an indication that no body is present.

7. The method according to claim 6, wherein in response to determining that the location comprises an indication that no body is present, updating the stored background values comprises:
   determining if there is a correlation between the differences between the sensor data and the predicted sensor values for each of the plurality of thermopiles and in response to identifying a correlation, updating the stored background values to be equal to the sensor data.

8. The method according to claim 6, wherein in response to determining that the location comprises an indication that no body is present, updating the stored background values comprises:
   in response to determining that no body has been present for more than a predefined period of time, updating the stored background values to be equal to the sensor data.

9. The method according to claim 6, wherein the location of the body further comprises a distance of the body from the plurality of thermopiles.

10. The method according to claim 1, further comprising:
    storing an error correction value for each of the plurality of thermopiles;
    resetting the error correction values to be equal to the stored background values each time the stored background values are updated;
    incrementing the error correction values over time and/or in correspondence to features extracted from sensor data for two or more of the plurality of thermopiles; and
    in response to determining that the error correction value for any of the plurality of thermopiles equals the sensor data for that thermopile, updating the stored background value for the thermopile to be equal to the sensor data for that thermopile.

11. The method according to claim 1, further comprising:
in response to detecting a change in the sensor data, determining if the body is present;
and wherein the method comprises:
in response to determining that the body is present, determining a location of the body based on differences between the sensor data and sensor values predicted using a forward model and the stored background values for each field of view; and updating the stored background values based on differences between the sensor data and the predicted sensor values; and
in response to determining that the body is not present, updating the stored background values based on the sensor data.

12. A system for detecting presence and location of a body using a mobile computing device, the system comprising:
a plurality of thermopiles coupled to the mobile computing device, each thermopile having a different field of view;
a location detection module;
a forward model; and
a data store arranged to store a background value for each of the plurality of thermopiles,
wherein the location detection module is arranged to receive sensor data from the plurality of thermopiles and in response to detecting a change in the sensor data, to access the stored background values for each field of view, determine using a forward model, sensor values corresponding to locations of the body by applying the sensor data to a lookup table within the forward model, determine a location of the body based on differences between sensor values within the sensor data and the determined sensor values from the forward model, and the differences between the sensor data and the stored background values; and to update the stored background values based on differences between the sensor data and the determined sensor values.

13. The system according to claim 12, wherein the location of the body is determined by reducing the differences between the sensor data and sensor values predicted using the forward model and the stored background values for each field of view.

14. The system according to claim 12, wherein the stored background values are updated by changing the stored background values to reduce the differences between the sensor data and sensor values predicted using the forward model and the stored background values for each field of view for the body at the determined location.

15. The system according to claim 12, wherein the system further comprises a motion sensor and wherein the location detection module is further arranged to update the stored background values in response to motion sensor data.

16. The system according to claim 12, further comprising a plurality of lenses and wherein the lenses are positioned in front of the plurality of thermopiles.

17. The system according to claim 12, further comprising a display device and wherein the plurality of thermopiles are integrated into or mounted on the display device.

18. The system according to claim 12, wherein the forward model comprises a lookup table arranged to store a value for a maximum forward contribution of the body to the sensor values and a plurality of values detailing the effect of the foreground contribution of the body at different locations relative to the plurality of thermopiles.

19. The system as claimed in claim 12, the location detection module being at least partially implemented using hardware logic selected from any one or more of: a field-programmable gate array, a program-specific integrated circuit, a program-specific standard product, a system-on-a-chip, a complex programmable logic device.

20. A computing device for detecting presence and location of a body, the computing device comprising:
an input for receiving sensor data from a plurality of thermopiles coupled to the computing device, each thermopile having a different field of view;
a processor; and
memory configured to store background values for each of the plurality of thermopiles, data defining a forward model and computer executable instructions, which when executed cause the processor, in response to detecting a change in the sensor data, to:
access the stored background values for each field of view;
determine, using a forward model, sensor values corresponding to locations of the body by applying the sensor data to a lookup table within the forward model;
determine a location of the body based on differences between sensor values within the sensor data and the determined sensor values from the the forward model, and the differences between the sensor data and the stored background values; and
update the stored background values based on differences between the sensor data and the determined sensor values.

* * * * *